United States Patent [19]
Durrett et al.

[11] Patent Number: 5,563,518
[45] Date of Patent: Oct. 8, 1996

[54] METHOD OF STANDARD DIELECTRIC WATER CUT MEASUREMENT WITH SMALL GAS FRACTION PRESENT

[75] Inventors: Michael G. Durrett; Wayne F. Warren, both of Houston; Raymond C. Hedges, Humble; Gregory J. Hatton, Houston, all of Tex.

[73] Assignee: Texaco Inc., White Plains, N.Y.

[21] Appl. No.: 270,353

[22] Filed: Jul. 5, 1994

[51] Int. Cl.⁶ .................................................. G01R 27/26
[52] U.S. Cl. ........................... 324/672; 324/684; 324/679; 73/19.01; 73/19.1
[58] Field of Search ........................... 73/881.04, 19.09, 73/19.1, 19.11, 19.01; 324/669, 720, 665, 664, 672, 679, 684

[56] References Cited

U.S. PATENT DOCUMENTS

| | | | |
|---|---|---|---|
| 3,518,982 | 7/1970 | Timmins | 73/19.1 |
| 4,014,206 | 3/1977 | Taylor | 73/19.1 |
| 4,751,842 | 6/1988 | Ekrann | 73/861.04 |
| 4,760,742 | 8/1988 | Hatton | 73/861.04 |
| 4,860,591 | 8/1989 | Garland | 73/861.04 |
| 4,974,452 | 12/1990 | Hunt | 73/861.04 |
| 4,975,645 | 12/1990 | Lucas | 73/861.04 |
| 5,049,823 | 9/1991 | Castel | 73/861.04 |
| 5,095,758 | 3/1992 | Cox | 73/861.04 |

*Primary Examiner*—Kenneth A. Wieder
*Assistant Examiner*—Jose M. Solis
*Attorney, Agent, or Firm*—James L. Bailey; Kenneth R. Priem; Russell J. Egan

[57] ABSTRACT

The gas fraction and the slip velocity are proportional to the difference in dielectric readings taken in a vertically upward flowing stream of oil/water/gas and in a vertically downwardly flowing stream of the same mixture. Actual water cuts are obtained by appropriately adjusting the dielectric water cut readings.

4 Claims, 1 Drawing Sheet

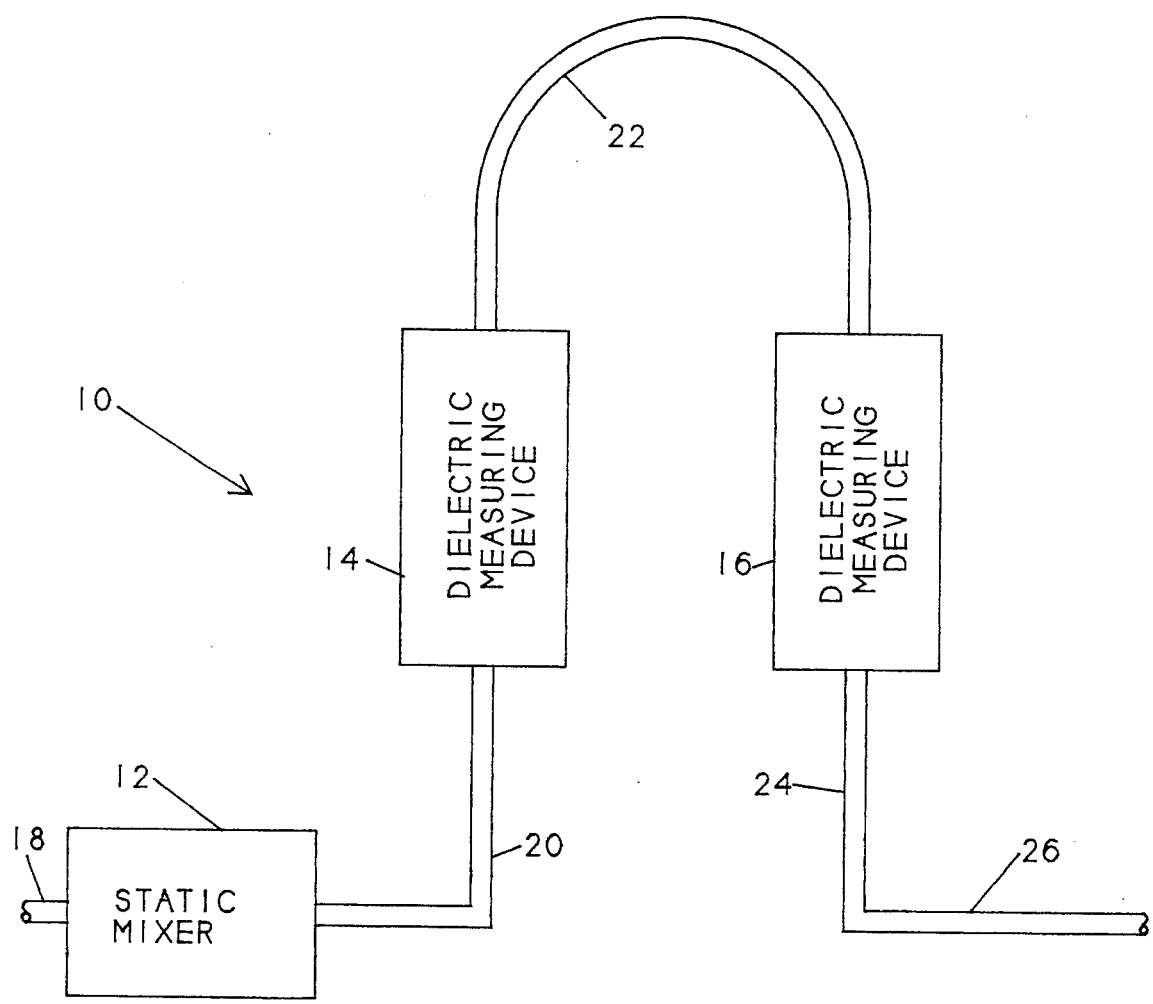

METHOD OF STANDARD DIELECTRIC WATER CUT MEASUREMENT WITH SMALL GAS FRACTION PRESENT

BACKGROUND OF THE INVENTION

1. The Field of the Invention

The present invention concerns a method and apparatus which will correct for the effect of small amounts of gas present during dielectric measurement of oil and water mixtures by using the slip velocity of the free gas.

2. The Prior Art

In a typical oil field application, water cut determination is performed by measuring the composite dielectric of a flowing mixture of oil and water. An example of this can be found in U.S. Pat. No. 4,873,648, the disclosure of which is incorporated herein by reference. Because of the large difference in the dielectric constants of water and oil, this is a sensitive method of water cut determination and is easily performed with such conventional instruments as capacitance probes. This measurement method requires only that the flow be well mixed, the oil in continuous phase, and assumes that no free gas is present. The limitation of "no free gas" is necessary because typical dielectric instruments perform only a single dielectric measurement while the variables determining the composite dielectric constant comprise both the water fraction as well as the gas fraction.

The prerequisite that there be no free gas is often violated, at least to a small degree, in most separator systems dealing with live crude oil. The present invention proposes a method and apparatus to reduce errors in water cut measurements due to free gas as well as obtaining a measure of free gas present.

SUMMARY OF THE INVENTION

The present invention corrects dielectric water cut measurements when small amounts of gas are present. Typical measurements involve bulk dielectric measurement. When a third component, such as gas, is present, this leads to errors in determination of water cut. The subject method corrects for the effects of a small amount of gas. Because of slip, a dielectric measurement in a vertical upward flowing stream of oil/water/gas will see a smaller contribution from gas than will a dielectric measurement in a vertical downward flowing stream of the same oil/water/gas mixture. This difference is proportional to the gas fraction and the slip velocity.

BRIEF DESCRIPTION OF THE DRAWINGS

The present invention will now be described, by way of example, with reference to the accompanying drawings in which the single FIGURE is a schematic side elevation of an apparatus incorporating the present invention.

DETAILED DESCRIPTION OF THE PREFERRED EMBODIMENT

The single FIGURE is a schematic side elevation of an apparatus adapted to carry out the present invention. The apparatus 10 includes a horizontal static mixer 12 and first and second vertically positioned dielectric metering devices 14, 16. The static mixer 12 is connected between a fluid input pipe 18 and an outlet pipe 20. The pipe 18 is connected to a source (not shown) while the pipe 20 is connected to the lower end of the first vertically positioned dielectric metering means 14. An inverted U-shaped pipe 22 interconnects the upper end of the first dielectric metering means 14 to the upper end of the second dielectric metering device 16. Outlet pipe 24 is connected to the lower end of the second dielectric metering means and becomes outlet flow means 26.

The invention is operated by flowing the multi-phase mixture, such as a gas/water/oil mixture, into the pipe 18, through the static horizontal mixer 12. The horizontal static mixer 12 insures good mixing of the fluids prior to taking the measurement. The fluid flow is then directed upwards through the pipe 20 and first dielectric metering device 14, around the loop 22, down through the second dielectric measuring device 16 and outlet pipe and out the outlet means 26.

If free gas is present, the signals from the two dielectric measuring devices 14, 16 will differ by an amount proportional to the free gas fraction and the average slip velocity of the free gas. The slip velocity is defined as the difference in velocity between the free gas and the liquid mixture. For small free gas fractions in this system, the magnitude of the slip velocity is equal to the rise velocity of a small bubble in a large quiescent container and is easily obtained from literature. Once the free gas fraction is known it is an easy matter to correct the dielectric measurements to obtain the actual water cuts. This is typically done using known mixture dielectric formulas, such as Hanai's equation.

Alternatively, the difference in the signals may be correlated in the laboratory with known gas fractions and water cuts.

The dielectric metering devices of the present invention can be selected from any of the well known devices, such as that described in the above mentioned U.S. Pat. No. 4,873,648, the disclosure of which is incorporated herein by reference.

The present invention may be subject to many modifications and changes without departing from the spirit or essential characteristics thereof. The present embodiment should therefor be considered in all respects as illustrative and not restrictive as to the scope of the present invention as defined by the appended claims.

We claim:

1. A method for substantially eliminating errors in water cut measurements, due to the presence of small amounts of gas in the mixture, comprising the steps of:

providing a horizontal static mixer;

providing first and second vertically positioned dielectric measuring means connected in series with the static mixer;

flowing the mixture through the static mixer, upwards through the first dielectric measuring means and downward through the second dielectric measuring means; and measuring the flow through said dielectric measuring means whereby the difference in these measurement will be the proportional to the gas present in the fluid.

2. An apparatus for substantially eliminating errors in fluid flow water cut measurements in a fluid pipeline due to the presence of small amounts of gas in a fluid mixture, said apparatus comprising in a series flow relationship:

horizontally disposed, mixer means in said fluid pipeline for mixing all phases of fluid flow in said pipeline;

first and second vertically positioned dielectric measuring means; and means connecting said mixer means and said dielectric measuring means in a series flow relationship to each other for flowing multi-phase fluid sequentially through said mixer means and each of said dielectric measuring means in opposite flow directions, whereby multi-phase fluid is first thoroughly mixed and then successively measured by said measuring means with a difference in fluid dielectric measurement being indicative of the amount of gas present in said fluid.

3. The apparatus according to claim 2 wherein said mixer is a static mixer.

4. The apparatus according to claim 2 wherein said first and second dielectric measuring means are positioned vertically in a parallel spaced relation to each other and wherein said multi-phase fluid flow is directed upward through said first dielectric measuring means and downward through said second dielectric measuring means.

* * * * *